United States Patent [19]

Konrad et al.

[11] Patent Number: 4,755,188
[45] Date of Patent: Jul. 5, 1988

[54] AGENT AND PROCESS FOR THE COLORING OF HAIR

[75] Inventors: Eugen Konrad, Darmstadt, Fed. Rep. of Germany; Hans-Jürgen Braun, Marly; Herbert Mager, Fribourg, both of Switzerland

[73] Assignee: Wella Aktiengesellschaft, Darmstadt, Fed. Rep. of Germany

[21] Appl. No.: 5,256

[22] Filed: Jan. 20, 1987

Related U.S. Application Data

[63] Continuation of Ser. No. 349,089, filed as PCT EP81/00057, May 27, 1981, published as WO82/00092, Jan. 21, 1982, abandoned.

[30] Foreign Application Priority Data

Jul. 7, 1981 [DE] Fed. Rep. of Germany ....... 3025715

[51] Int. Cl.$^4$ .................................................. A61K 7/13
[52] U.S. Cl. .................................................. 8/408; 8/424
[58] Field of Search .................................... 8/408, 424

[56] References Cited

U.S. PATENT DOCUMENTS 3,563,684  2/1971  Charle et al. ........................ 8/410
4,279,613  7/1981  Konrad et al. ...................... 8/408

FOREIGN PATENT DOCUMENTS 1220631  1/1971  United Kingdom .
1334817  10/1973  United Kingdom .

OTHER PUBLICATIONS

Beilstein 4, Band 6, 1923, p. 903,6.
Beilstein 4, Band 6, 1931, p. 448,6.

*Primary Examiner*—Albert T. Meyers
*Assistant Examiner*—John M. Kilcoyne
*Attorney, Agent, or Firm*—Michael J. Striker

[57] ABSTRACT

A composition and process are disclosed for oxidative coloring of hair on the basis of at least one substituted phenol of the general formula

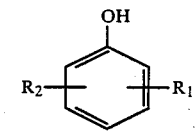

whereby $R_1$ represents a hydroxy alkyl group with 1 to 4 carbon atoms and $R_2$ a hydrogen atom or alkyl group with 1 to 4 carbon atoms, or the phenolate thereof, as a coupler substance. The inventive coupler substance, of which 2-hydroxy-methyl-5-methyl-phenol and 3-(β-hydroxy ethyl)-6-methyl-phenol are preferred, should be present in a concentration of about 0.01 to 3.0% by weight, in particular 0.1 to 2.0% by weight. The described coupler substances are active as blue couplers. The obtained color shades are stable, resistant to wear and very well reproducible. They have very favorable characteristics with respect to toxicology and dermatology and do not give the colored hair an unpleasant, penetrating cresolic aroma. The process involves forming an oxidizable developer-coupler combination of a developer substance with the substituted phenol as coupler substance, and an oxidation agent, applying a coloring-effective amount of the combination onto human hair, rinsing the hair after about 10–45 minutes at a temperature between 15° and 50° C., and drying the hair.

10 Claims, No Drawings

AGENT AND PROCESS FOR THE COLORING OF HAIR

This is a continuation of application Ser. No. 349,089, filed as PCT EP81/00057, May 27, 1981, published as WO82/00092, Jan. 21, 1982, and now abandoned.

The invention relates to a composition and a process for coloring of hair on the basis of a substituted phenol of the general formula

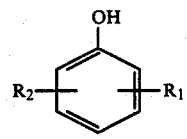

whereby $R_1$ represents a hydroxy alkyl group with 1 to 4 carbon atoms and $R_2$ represents a hydrogen atom or an alkyl group with 1 to 4 carbon atoms as a coupler substance.

Mainly, 1,4-diamino benzene, 2,5-diamino toluene, 3-methyl-4-amino-phenol and p-amino phenol are used as developer substances. The preferred used coupler substances are α-naphthol, resorcinol, 4-chloro resorcinol, 2-methyl resorcinol, m-amino phenol, 5-aminocresol and derivatives of m-phenyl diamine, like m-toluylene diamine and 2,4-diamino-anisole. These derivatives, as well as the m-phenylene diamine itself are obtained as so-called blue couplers which generate blue shades during the oxidative coupling with 1,4 diamino benzene or 1,4-diamino benzene derivatives.

Particular requirements must be met by the oxidation coloring compositions which are used for coloring human hair. They should be harmless from the toxicological and dermatological point of view and should enable a coloring in the desired intensity. Further more, it is required that a wide variety of different color nuances can be generated by combination of suitable developer and coupler components. Furthermore, a good light, permanent waving, acid and friction resistance is required for the obtainable hair colorings. In any case, such hair colorings must remain stable over a time period of at least 4 to 6 weeks without reaction of light, chemical agents and friction.

The m-phenylene diamine which is presently used as a blue coupler in hair coloring compositions, whose derivative m-toluylene diamine and 2,4-diamino anisole, as well as the recently recommended blue coupler as, for example, 1-hydroxy-3-amino-6-chloro benzene and 2,4-diamino phenoxy ethanol, cannot satisfactorily meet the aforementioned requirements.

It was therefore an object to look for a hair coloring composition, as well as a hair coloring process, wherein the requirements are met in an optimum manner.

It was found that compositions for oxidative coloring of hair which have a combination of known developer substances in hair colorings with at least one substituted phenol of the general formula

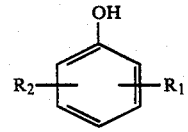

whereby $R_1$ represents a hydroxy alkyl group with 1 to 4 carbon atoms and $R_2$ a hydrogen atom or an alkyl group with 1 to 4 carbon atoms, also in form of the phenolate with organic or inorganic bases, contained as coupler substance, do meet the requirements asked for in an excellent manner.

The substituted phenols of the stated formula which are contained as coupler substances in the inventive hair coloring compositions are very well water soluble by adding alkalies, for example, sodium hydroxide and also have an unexpected good storage stability, in particular as a component of the inventive hair coloring composition.

Examples for suitable coupler substances of the stated formula contained in the inventive hair coloring composition are, in particular 3-(β-hydroxyethyl)-phenol
3-(γ-hydroxypropyl)-phenol
3-(β-hydroxyethyl)-6-methyl-phenol
2-(β-hydroxyethyl)-5-methyl-phenol
2-hydroxymethyl-5-methyl-phenol
2-hydroxymethyl-6-methyl-phenol The mentioned coupler substances of which 2-hydroxymethyl-5-methyl-phenol and 3-(β-hydroxyethyl)-6-methyl-phenol are preferred in the hair coloring compositions, should be present in a concentration of 0.01 to 3.0% by weight, in particular 0.1 to 2.0% by weight.

Furthermore, the hair coloring compositions may contain additional known coupler substances, in particular α-napthol, 3,4 diaminobenzoic acid, resorcinol, 4-chloro resorcinol, 2-methyl resorcinol, 4-amino phenol and 3-amino-6-methyl-phenol. Furthermore, 4-oxy-1,2-methylene dioxybenzene and 4-amino-1,2-methylene dioxybenzene may be advantageously used as a coupler substance.

Of all the known developer substances the following, preferably, are taken into consideration as a component of the inventive hair coloring agent, 1,4-diamino benzene, 2,5-diamino toluene, 2,5-diamino anisole, p-aminophenol as well as 3-methyl-4-aminophenol. Also, 2,5-diamino benzyl alcohol and 2-(β-hydroxyethyl)-1,4-diaminobenzene are advantageously usable as a developer substance.

According to the present invention the substituted phenols of the stated formula as well as the known coupler and developer substances may be present in the hair coloring compositions either alone or in an admixture.

The total amount of the developer substance-coupler substance combination contained in the described hair coloring compositions should be about 0.1 to 5.0% by weight, in particular 0.5 to 3.0% by weight.

Generally, the developer components are used in equimolar amounts in relationship to the coupler components. However, it is not disadvantageous if the developer component is present at a certain higher or lower level.

Furthermore, the hair coloring compositions of this application may contain additional other color components, for example, 6-amino-3-methyl-phenol, 6-amino-2-methyl-phenol and 6-amino-3-ethoxy-phenol, as well as usual direct dyes, for example, triphenylmethandyes, like Diamond Fuchsin (C.I. 42 510) and Leather Ruby HF (C.I. 45 520), aromatic nitro dyes, like 2-nitro-1,4-diamino benzene and 2-amino-4-nitrophenol, azo dyes, like Acid Brown 4 (C.I. 14 805) and Acid Blue 135 (C.I. 13 385), anthraquinone dyes, like Disperse Red 15 (C.I. 60 710) and Disperse Violet 1 (C.I.61,100), furthermore 1,4,5,8-tetraamino-anthraquinone and 1,4-diamino-anthraquinone.

In addition, other usual cosmetic additives may be contained in the hair coloring compositions, for example, antioxidants, like ascorbic acid or sodium sulfite, perfume oils, complex formers, wetting agents, emulsifiers, thickeners, hair caring ingredients and others.

The prepared product may be in form of a solution, preferably a creme, a gel or an emulsion. Its composition represents a mixture of the dye components with the components which are usual for such preparations. As usual components of cremes, emulsions or gels, for example, wetting agents or emulsifiers are considered from the classes of the anionic, cationic or nonionogenic surface active substances, like fatty alcohol sulfates, alkylsulfonates, alkyl trimethyl ammonium salts, oxethylized fatty alcohols, oxethylized nonylphenols, fatty acids alkanolamides, furthermore, thickeners, like higher fatty alcohols, starch, cellulose derivatives, paraffine oil and fatty acids, as well as caring agents, like lanoline derivatives, cholesterine and pantothene acid. The mentioned components are used in amounts which are usual for such purposes, for example, the wetting agent and the emulsifiers in concentrations of about 0.5 to 30% by weight, while the thickener may be contained in an amount of about 0.1 to 25% by weight in the preparations.

Depending on the composition the inventive hair coloring compositions may react lightly acid, neutral or alkaline. In particular they have a pH-value in the alkaline range between 8.0 and 11.5, whereby the adjustment is preferably carried out with ammonia. However, organic amines may be used, for example, monoethanolamine or triethanolamine.

In the inventive process for the oxidative coloring of hair one admixes the hair coloring compositions, which are a combination of the developer substances known in hair coloring with at least one substituted phenol of the stated formula as a coupler substance which also may contain added coupler substances, with an oxidation agent shortly before use and applies this mixture to the hair. Mainly hydrogen peroxide is considered as an oxidation agent for developing the hair coloring, for example, as a 6% aqueous solution or its addition compounds of urea, melamine or sodium borate. One permits the mixture to react on the hair at 15° to 50° C. for about 10 to 45 minutes, preferably for 30 minutes, subsequently rinsing the hair with water and dry it. If need be, the hair is washed with a shampoo subsequent to this rinsing and, if need be, again rinsed with a weak organic acid, for example, citric acid or tartaric acid.

The substituted phenols in accordance with the formula contained in the compositions according to the invention are known compounds or compounds which can be made in accordance with the usual organic synthesis processes described in the literature.

For example, when making 2-hydroxymethyl-5-methyl-phenol one starts with the m-cresotic acid which is available in technical quantities and which is transformed into the corresponding cresotic acid ester by means of esterification [1] and reduced [2] with lithium aluminum hydride. In the same manner one can make 2-hydroxymethyl-6-methyl-phenol from o-cresotic acid.

(1) Houben-Weyl, Methoden der Organischen Chemie, 4.Auflage, VIII, 525
(2) Organikum, VEB Deutscher-Verlag der Wissenschaften, Berlin (1976) 614 Organic Reactions 6 (1951)469

For synthesis of 3-($\beta$-hydroxyethyl)-6-methyl-phenol, 4-methylphenyl acetic acid is compounded by nitration to 4-methyl-3-nitrophenyl acetic acid. Subsequently, the selective reduction [3] of the carboxyl group with borohydride is carried out, whereby 2-(4'-methyl-3' nitro-phenyl)-ethanol is obtained. Thereafter, the nitro group is reduced to the amino-group with hydrogen in the presence of a platinum catalyst. Finally, the amino group is replaced by an OH-group during the compounding with salpetric acid by eliminating nitrogen.

(3) H. C. Brown, B. C. Subba Rao. J. Am. Chem Soc. 82 (1960) 681

With respect to the coloring possibilities, the inventive hair color compositions offer a wide variety of different color nuances, depending on the type and composition of the color components, which extend from blonde to brown, ash, purple, violet, golden to the blue as well as mat color shades. Thereby, the color shades are characterized by their special stability and wearing stability. The observed coloring result is independent from the structure of dyed hair. This means that the color shades obtained with the inventive hair coloring compositions are very well reproducible.

Furthermore, the progress obtained by the use of the substituted phenols of the stated formula in the described hair coloring compositions are very important with respect to toxicology and dermatology, for example, with respect to the known blue couplers 2,4-diamino toluene, 2,4-diamino anisole and 1,3-diamino benzene, whereby this progress is based on the two hydroxyl groups contained in the substituted phenols (in case that $R_1$ represents a hydroxy alkyl group and the reduction of the lipoid solubility connected therewith.

Furthermore, it is very important that for the first time new blue couplers are present with some of the described phenols in accordance with the formula, for example, 2-hydroxy methyl-5-methyl-phenol, which in contrast to couplers of a similar structure formula, for example, 2,5-dimethyl phenol and m-cresol, surprisingly does not give the colored hair an unpleasant, penetrating cresolic aroma.

Finally, a coloring of gray hair, which is chemically not damaged, is made possible without any problems and with a good covering power.

The subsequent examples shall explain the subject matter of the invention in greater detail.

EXAMPLES

EXAMPLE 1

Hair coloring composition in gel form

| | |
|---|---|
| 0.40 g | 2-hydroxymethyl-5-methyl-phenol |
| 0.70 g | 2,5-diamino toluene sulfate |
| 0.12 g | sodium hydroxide, solid |
| 0.30 g | ascorbic acid |
| 1.00 g | hydroxy ethyl cellulose, highly viscous |
| 5.00 g | lauryl alcohol-diglycol ether sulfate, sodium salt |
| 10.00 g | ammonia, 22% |
| 82.48 g | water |
| 100.00 g | |

50 g of the aforementioned hair coloring composition was admixed with 50 ml hydrogen peroxide solution (6%) shortly before use and the mixture was then applied onto blonde human hair. After a reaction time of 30 minutes at about 40° C. the hair is rinsed with water and dried. The hair is colored with an intensive blue shade.

EXAMPLE 2

Hair coloring composition in gel form

| | |
|---|---|
| 0.40 g | 2-hydroxymethyl-5-methyl-phenol |
| 0.80 g | 2,5-diamino benzyl alcohol-dihydrochloride |
| 0.12 g | sodium hydroxide, solid |
| 0.30 g | ascorbic acid |
| 15.00 g | oleic acid |
| 7.00 g | isopropanol |
| 10.00 g | ammonia, 22% |
| 66.38 g | water |
| 100.00 g | |

Shortly before use 50 g of this hair coloring composition is admixed with 50 ml hydrogen peroxide solution (6%) and the mixture is reacted on blonde human hair for about 30 minutes at 40° C. Thereafter, the hair is rinsed with water and dried. The hair has received a gray-violet-bluish coloration.

EXAMPLE 3

Hair coloring composition in creme form

| | |
|---|---|
| 0.15 g | 2-hydroxymethyl-5-methyl-phenol |
| 0.80 g | 2,5-diamino toluene sulfate |
| 0.20 g | resorcinol |
| 0.04 g | m-aminophenol |
| 0.05 g | sodium hydroxide, solid |
| 3.50 g | lauryl alcohol-diglycol ether sulfate, sodium salt (28% watery solution) |
| 0.30 g | sodium sulfide, free of water |
| 15.00 g | cetyl alcohol |
| 5.00 g | ammonia, 22% |
| 74.96 g | water |
| 100.00 g | |

50 g of this hair coloring composition was admixed with 50 ml hydrogen peroxide solution (6%) shortly before use and the mixture was applied onto blonde human hair. After a reaction time of 30 minutes at 40° C. the hair is rinsed with water and dried. The hair is colored light ash brown.

All percentage numbers stated in the application represent weight by percentage.

We claim:

1. An aqueous composition for oxidative coloring of human hair, comprising 0.1 to 5.0% by weight of an oxidative developer-coupler combination comprising 0.01 to 3.0% by weight of a substituted phenol of the formula

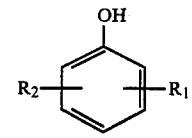

wherein $R_1$ represents a hydroxyalkyl group having 1 to 4 carbon atoms and $R_2$ represents a hydrogen atom or an alkyl group having 1 to 4 carbon atoms, as a coupler substance.

2. The composition of claim 1, wherein the coupler substance is present in a concentration of 0.1 to 2.0% by weight.

3. The composition of claim 1, wherein the developer substance-coupler substance combination is present in a total amount of 0.5 to 3.0% by weight.

4. The composition of claim 1, containing a color component selected from the group consisting of 6-amino-3-methyl-phenol, 6-amino-2-methyl-phenol and 6-amino-3-ethoxy-phenol.

5. The composition of claim 1, containing an antioxidant selected from the group consisting of ascorbic acid and sodium sulfite.

6. The composition of claim 1, characterized in that it contains a developer substance selected from the group consisting of 1,4-diamino-benzene, 2,5-diamino-toluene, 2,5-diamino-anisole, 2-(β-hydroxyethyl)-1,4-diamino-benzene, 2,5-diamino-benzyl alcohol, p-aminophenol and 3-methyl-4-aminophenol.

7. The composition of claim 1, characterized in that it contains a coupler substance selected from the group consisting of α-naphthol, 3,4-diamino-benzoic acid, resorcin, 4-chlorine-resorcin, 2-methyl-resorcin, m-aminophenol, 3-amino-6-methyl-phenol, 4-oxy-1,2-methylenedioxy-benzene and 4-amino-1,2-methyl-enedioxy-benzene.

8. The composition of claim 1, wherein the substituted phenol is selected from the group consisting of 3-(β-hydroxy ethyl)-phenol, 3-(β-hydroxypropyl)-phenol, 3-(β-hydroxy ethtyl)-6-methyl-phenol, 2-(β-hydroxy ethyl)-5-methyl-phenol, 2-hydroxymethyl-5-methyl-phenol and 2-hydroxy methyl-phenol.

9. The composition of claim 1, containing a color component selected from the group consisting of Diamond Fuchsin (C.I. 42 510), Leather Ruby HF (C.I. 42 520), 2-nitro-1,4-diamino-benzene, 2-amino-4-nitro-phenol, Acid Brown 4 (C.I. 14 805), Acid Blue 135 (C.I. 13 385), Disperse Red 15 (C.I. 60 710), Disperse Violet 1 (C.I. 61 100), 1,4,5,8-tetra amino anthraquinone and 1,4-diamino-anthraquinone.

10. The process of oxidative coloring of human hair, comprising forming a composition according to claim 1; admixing said composition with an aqueous solution of an oxidation agent selected from the group consisting of hydrogen peroxide and its addition compound with urea, melamine or sodium borate; applying a sufficient amount for coloring the hair of said mixture to human hair; allowing the mixture to react on the hair between about 10 to 45 minutes at a temperature between 15° and 50° C.; rinsing the hair and drying the hair.

* * * * *